(12) United States Patent
Miyama et al.

(10) Patent No.: US 8,237,012 B2
(45) Date of Patent: Aug. 7, 2012

(54) ABSORBENT ARTICLE

(75) Inventors: Takuya Miyama, Kagawa (JP); Jun Kudo, Kagawa (JP); Chiemi Habu, Kagawa (JP); Kumiko Nishikawa, Kagawa (JP)

(73) Assignee: Uni-Charm Corporation, Kawanoe-shi (JP)

( * ) Notice: Subject to any disclaimer, the term of this patent is extended or adjusted under 35 U.S.C. 154(b) by 133 days.

(21) Appl. No.: 11/533,479

(22) Filed: Sep. 20, 2006

(65) Prior Publication Data

US 2007/0073253 A1   Mar. 29, 2007

(30) Foreign Application Priority Data

Sep. 26, 2005   (JP) .................. 2005-278764

(51) Int. Cl.
*A61F 13/15* (2006.01)
*A61F 13/20* (2006.01)

(52) U.S. Cl. ............... 604/378; 604/358; 604/385.01; 604/385.101; 604/385.23; 604/379

(58) Field of Classification Search ............... 604/379, 604/380, 383, 385.01, 385.23, 385.101, 378, 604/317, 358
See application file for complete search history.

(56) References Cited

U.S. PATENT DOCUMENTS

| | | | | |
|---|---|---|---|---|
| 3,017,304 A | * | 1/1962 | Burgeni ................. | 428/167 |
| 4,184,498 A | * | 1/1980 | Franco .................. | 604/375 |
| 4,501,586 A | * | 2/1985 | Holtman ............... | 604/380 |
| 4,585,448 A | * | 4/1986 | Enloe .................. | 604/378 |
| 4,600,620 A | * | 7/1986 | Lloyd et al. ............ | 428/195.1 |
| 4,603,069 A | * | 7/1986 | Haq et al. .............. | 428/76 |
| 4,624,666 A | * | 11/1986 | DeRossett et al. ........ | 604/366 |
| 4,886,697 A | * | 12/1989 | Perdelwitz et al. ....... | 428/192 |
| 5,486,167 A | * | 1/1996 | Dragoo et al. .......... | 604/384 |
| 5,507,735 A | * | 4/1996 | Van Iten et al. ......... | 604/385.05 |
| 5,545,156 A | * | 8/1996 | DiPalma et al. ......... | 604/385.23 |
| 5,562,650 A | * | 10/1996 | Everett et al. ........... | 604/378 |

(Continued)

FOREIGN PATENT DOCUMENTS

JP   11-113955   4/1999

(Continued)

OTHER PUBLICATIONS

University of Cambridge, DoITPoMS Teaching and Learning Packages, "Crystallinity in polymers." Accessed Oct. 7, 2008. http://www.msm.cam.ac.uk/doitpoms/tlplib/polymers/stress-strain.php.*

(Continued)

*Primary Examiner* — Leslie Deak
*Assistant Examiner* — Adam Marcetich
(74) *Attorney, Agent, or Firm* — Morrison & Foerster LLP

(57) ABSTRACT

An absorbent article having a substantially oblong shape, which is superior in liquid-proof performance and fitness, includes a liquid permeable top sheet, a back sheet, an absorbent body having elasticity disposed between the top sheet and the back sheet, and a compressed portion compressing the top sheet and the absorbent body. The compressed portion is disposed continuously to form a protrusion in a longitudinal direction to define a substantially U shape. The absorbent portion has a low elasticity portion, disposed on one part of the absorbent body, and formed so that elasticity weakens when compression to a prescribed thickness is carried out. The low elasticity portion is disposed in the vicinity of an end protruding the most in the longitudinal direction of the substantially U shape.

6 Claims, 12 Drawing Sheets

U.S. PATENT DOCUMENTS

| | | | |
|---|---|---|---|
| 5,693,037 A * | 12/1997 | Lee et al. | 604/381 |
| 5,807,365 A * | 9/1998 | Luceri | 604/367 |
| 5,849,002 A * | 12/1998 | Carlos et al. | 604/378 |
| 6,140,551 A * | 10/2000 | Niemeyer et al. | 604/367 |
| 6,323,388 B1 * | 11/2001 | Melius et al. | 604/368 |
| 6,326,525 B1 * | 12/2001 | Hamajima et al. | 604/378 |
| 6,361,527 B1 * | 3/2002 | Van Gompel et al. | 604/385.25 |
| 6,409,715 B1 * | 6/2002 | Tanji | 604/385.19 |
| 6,437,214 B1 * | 8/2002 | Everett et al. | 604/378 |
| 6,506,961 B1 * | 1/2003 | Levy | 604/380 |
| 6,617,490 B1 * | 9/2003 | Chen et al. | 604/380 |
| 2002/0040211 A1 * | 4/2002 | Drevik | 604/380 |
| 2003/0018314 A1 * | 1/2003 | Nozaki et al. | 604/385.101 |
| 2003/0021952 A1 * | 1/2003 | Zink et al. | 428/137 |
| 2003/0088231 A1 * | 5/2003 | Yoshimasa et al. | 604/387 |
| 2003/0125691 A1 * | 7/2003 | Fernfors | 604/385.01 |
| 2003/0187417 A1 * | 10/2003 | Kudo et al. | 604/379 |
| 2004/0138637 A1 * | 7/2004 | Mishima et al. | 604/385.101 |
| 2004/0243087 A1 * | 12/2004 | Kinoshita et al. | 604/385.04 |
| 2004/0260260 A1 * | 12/2004 | Feller et al. | 604/385.01 |
| 2005/0148983 A1 * | 7/2005 | Doverbo et al. | 604/385.101 |
| 2006/0116653 A1 * | 6/2006 | Munakata et al. | 604/380 |
| 2006/0276767 A1 * | 12/2006 | Ueminami et al. | 604/385.31 |

FOREIGN PATENT DOCUMENTS

| | | |
|---|---|---|
| JP | 2000-14701 | 1/2000 |
| JP | 2001-008971 | 1/2001 |
| JP | 2001-299812 | 10/2001 |
| JP | 2003-24371 | 1/2003 |
| JP | 2003-180733 | 7/2003 |
| JP | 2004-8677 | 1/2004 |
| JP | 2004-089392 A | 3/2004 |
| JP | 2004-113538 | 4/2004 |
| JP | 2004-154154 | 6/2004 |
| JP | 2004-181084 | 7/2004 |
| JP | 2004-181085 A | 7/2004 |
| JP | 2004-350908 | 12/2004 |
| JP | 2005-007075 | 1/2005 |
| JP | 2005-007144 | 1/2005 |
| JP | 2005-177078 | 7/2005 |

OTHER PUBLICATIONS

Japanese Notice of Reasons for Rejection mailed Apr. 12, 2011, directed to counterpart Japanese Patent Application No. 2005-278764; 5 pages.

* cited by examiner

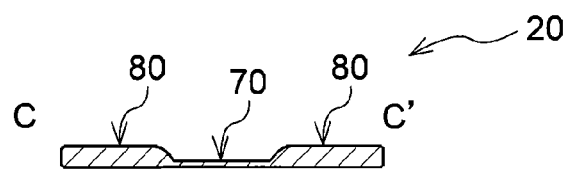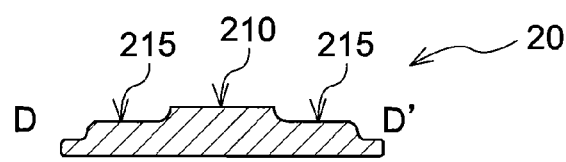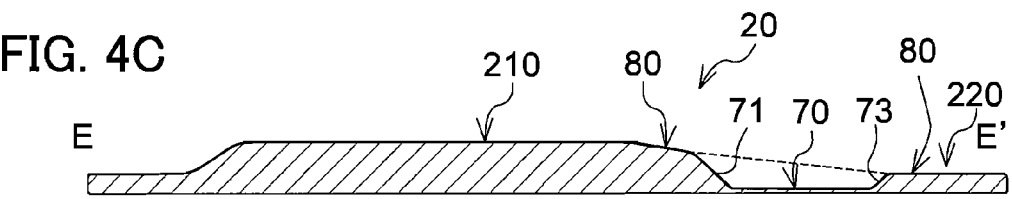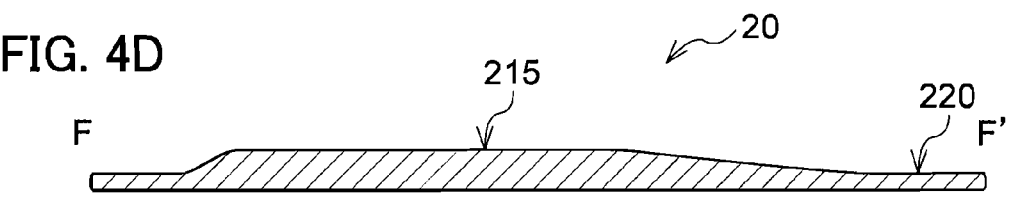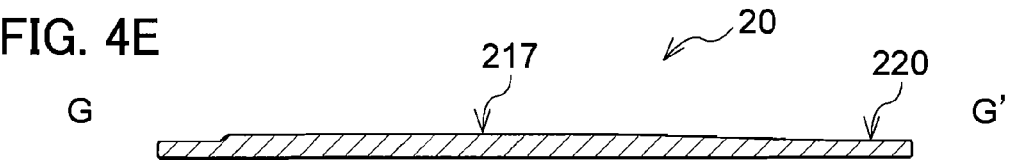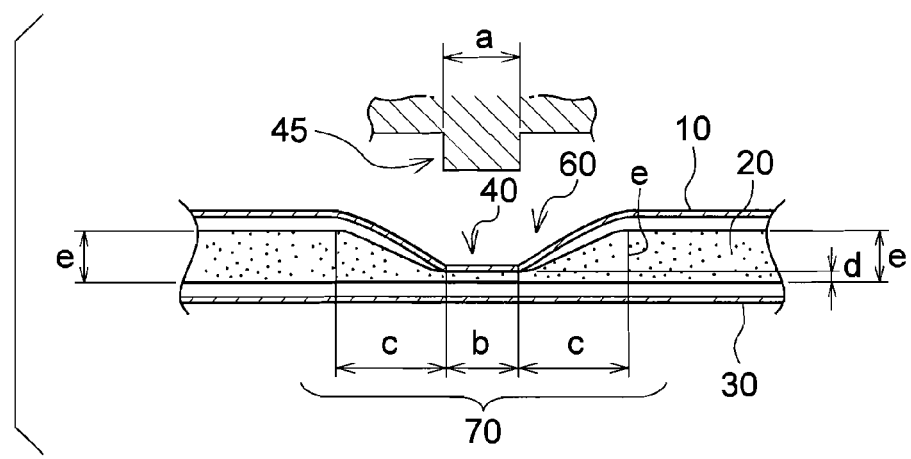

FIG. 6A
FIG. 6B
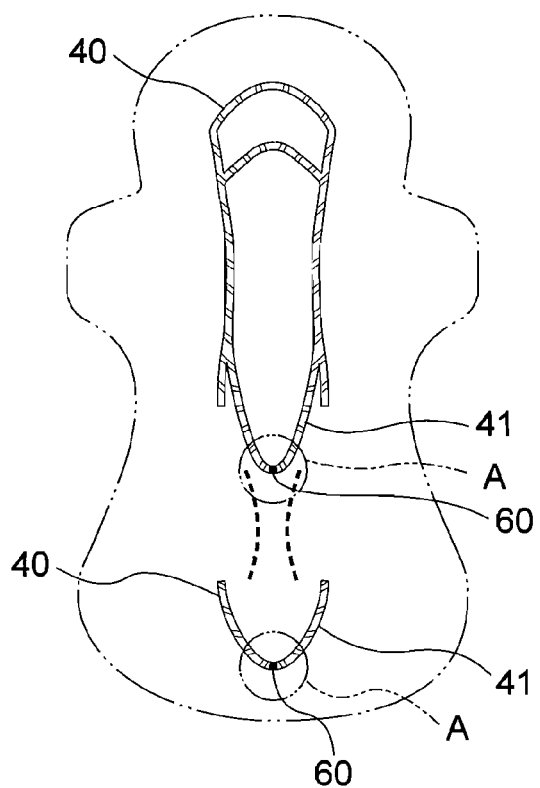
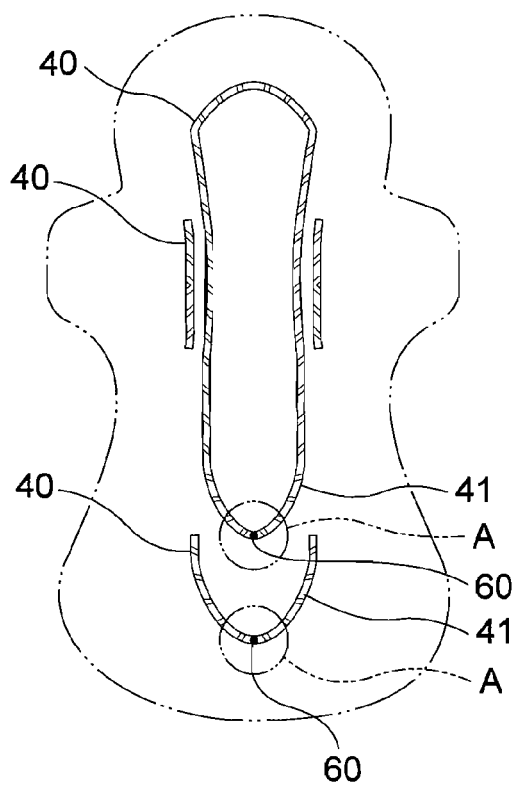

ABSORBENT ARTICLE

This application is based on and claims the benefit of priority under 35 U.S.C. §119 to Japanese Patent Application No. 2005-278764, filed on Sep. 26, 2005, the contents of which is incorporated herein by reference.

BACKGROUND OF THE INVENTION

1. Field of the Invention

The present invention relates to an absorbent article, such as a sanitary napkin, and the like, having a good sealing performance and fitting property, in which a liquid prevention groove is formed to prevent separation of a compressed part.

2. Related Art

Conventionally, an absorbent article is generally known to include an absorbent layer, a liquid permeable top sheet covering the surface of a wearer's skin, a liquid impermeable back sheet covering the surface of the absorbent layer on the side of the wearer's clothing. Such an absorbent article is generally worn in a state in which a back sheet is bonded through a pressure sensitive adhesion layer to the inner surface of the clothing in the crotch region of an undergarment. A liquid impermeable groove is formed through compression by continuously applying pressure to bond the top sheet and the absorbent layer, and to prevent leakage by controlling the once absorbed body fluid from dispersing and at the same time giving a wearer a better fitted feeling.

In this liquid-proof groove, an absorbent layer is formed by surrounding a predetermined region in the absorbent layer so that the liquid absorbed by the absorbent layer does not flow out. As for the absorbent article having a shape extended in a longitudinal direction, the shape of the liquid-proof groove may be substantially elliptical or a modified shape thereof. This substantially elliptical absorbent article is curved at the edges extending in the longitudinal direction to form an end at the far end of this curve, which projects outward in the longitudinal direction.

Since an absorbent layer is usually a material having elasticity, a compressed portion and the vicinity thereof have resiliency so that the absorbent layer recovers from a compressed state back to an original state, so that force acts in a direction tending to separate the compressed portion.

Here, a plurality of the liquid-proof grooves are formed in a widthwise direction by surrounding an absorbent layer as described above. In other words, a top sheet and the absorbent layer are held together by compression at multiple sites in the widthwise direction. However, at the end projected outwardly in a longitudinal direction with the substantially elliptical shape as described above, since in practice they are held together by compression at one point, separation can easily occur in comparison with the compressed portion in the other liquid-proof grooves.

In addition, in response to a wearer's feeling on wearing this absorbent article and desirable liquid-proof effects, various other absorbent articles have been suggested, in which a plurality of the liquid-proof grooves are formed. However, when a plurality of the liquid-proof grooves are formed as thus described, for example, when a large number of the liquid-proof grooves are present in a widthwise direction of the absorbent article, the pressure exerted on the compressed portion, formed by a predetermined compression process, becomes insufficient, while causing the depth of the liquid-proof grooves to become shallow, making separation occur even more easily. Separation of the compressed portion in the liquid-proof grooves lowers leakage prevention performance and wearability.

Furthermore, for example, an absorbent article described in Japanese Patent Application, Laid Open No. 2001-8971 has a liquid-proof grooves without being shallow, which are formed by widening the width of the liquid-proof grooves in a region with two or fewer liquid-proof grooves in the widthwise direction, by reducing the width of the liquid-proof grooves in a region with three or more liquid-proof grooves in the widthwise direction, and by building up a sufficient pressure that is added to the compressed portion formed by a compression process.

SUMMARY OF THE INVENTION

However, an absorbent article in which separation (lifting) is prevented at an end in a longitudinal direction of liquid-proof grooves formed in a substantially oval shape has not yet been proposed. In addition, Japanese Patent Application, Laid Open No. 2001-8971 discloses an absorbent article having liquid-proof grooves that are not shallow, formed by widening the width of the liquid-proof grooves in the region where less than or equal to two liquid-proof grooves are formed in the widthwise direction, by reducing the width of the liquid-proof grooves in the region where greater than or equal to three leakage prevention grooves are formed in the widthwise direction, and by building up a sufficient pressure that is added to the compressed portions formed by a compression process. However, reducing the width of the compressed portions will cause a compression to reduce as a result of decrease in the compressed (bonded) surface area between a top sheet and the absorbent layer, and thus the edges become easily separated (lifted). Separation of the compressed portions in the liquid-proof grooves lowers a liquid-proof performance and wearability. Based on the foregoing, these are objects of the present invention.

The present invention was made in view of the above problems. The present invention provides an absorbent article that is superior in liquid proof performance and wearability.

In order to achieve the above objects, the inventors have invented an absorbent article, as described below, in which, by lowering the elasticity of an absorbent layer in the vicinity of an end projected outwards in a longitudinal direction of liquid-proof grooves formed in a substantially oval shape, separation (lifting) of a compressed portion can be prevented.

In a first aspect of the invention, an absorbent article having a substantially oblong shape includes a liquid permeable top sheet, a back sheet, an absorbent body having elasticity, disposed between the top sheet and the back sheet, and a compressed portion compressing the top sheet and the absorbent body, extending in a longitudinal direction. The compressed portion is disposed continuously so as to form a substantially U shape protruding in a longitudinal direction of the absorbent article. The absorbent body is provided with a low elasticity portion disposed on a part of the absorbent body and formed so that elasticity, which is produced when compression to a prescribed thickness is carried out, weakens. The low elasticity portion is disposed in the vicinity of an end which protrudes the most in the longitudinal direction of the U shape.

According to the first aspect of the invention, the low elasticity portion is disposed in the compressed portion in the vicinity of the end where separation easily occurs. The low elasticity portion is formed such that the elasticity weakens when the portion is compressed at a predetermined thickness. In the compressed portion, liquid-proof grooves are configured continuously by having a projection extending in a longitudinal direction to define a substantially U shape. Therefore, separation in the compressed portion can be prevented by the elasticity of the absorbent body created in the vicinity of the end.

In a second aspect of the invention, an absorbent article according to the first aspect of the invention has a compression maintenance index greater than or equal to 80.

According to the second aspect of the invention, the compressed portion located at the end, having a compression maintenance index greater than or equal to 80, is seen as being not lifted when viewed from a top face of the compressed portion. Here, the compression maintenance index (k) is represented by a value which is calculated by dividing width (b) of the compressed portion having its thickness less than or equal to 0.5 mm, by the value of the width (a) in the compressed region for forming the compressed portion (for example, a convex potion formed on a compressed roll portion), which is multiplied by 100, as described later in formula 1.

In a third aspect of the invention, in an absorbent article according to the first or second aspects of the invention, the low elasticity portion is very thin with respect to an adjacent portion of the absorbent body disposed adjacent to the low elastic portions.

According to the third aspect of the present invention, the low elasticity portion is very thin with respect to the adjacent portion of an absorbent body disposed adjacent to the low elasticity portion, such that the elasticity with a resiliency created by compressing the low elastic portions at a predetermined thickness can be made low. Therefore, a separation of the compressed portion can be prevented by the elasticity created in the vicinity of the edge.

According to a fourth aspect of the invention, in the absorbent article according to any one of the first through third aspects of the invention, the low elasticity portion, centered on the end, having a diameter of 10 to 50 mm, forms a substantially circular shape.

According to the fourth aspect of the invention, the low elastic portion, centered on the end having a diameter of 10 to 50 mm, is formed in a substantially circular shape, and forms the low elasticity portion without excessively reducing the volume of the absorbent body, so that the absorbent body can suitably absorb the fluid. This enables prevention of separation of the compressed portion at the end and also facilitates fluid absorbency in the absorbent body.

In a fifth aspect of the invention, in an absorbent article according to any one of the first through the fourth aspects of the invention, the low elasticity portion, having a thickness at a distance 4 mm away from the end extending in the longitudinal direction is less than or equal to 2.5 mm.

According to the fifth aspect of the invention, the low elasticity portion, having a thickness, at a distance 4 mm in the longitudinal direction from the end, of less than or equal to 2.5 mm, which can create a weak resiliency (elasticity) in the vicinity of the end. This enables separation of the compressed portions in the end to be suitably prevented.

In a sixth aspect of the invention, in the absorbent article according to the third aspect of the invention, the absorbent material used to construct the absorbent body in the low elasticity portion, is used less in an adjacent portion.

According to the sixth aspect of the invention, the absorbent material used to construct an absorbent body in the low elasticity portion is used less in the adjacent portion, such that the elasticity in the vicinity of the compressed portions at the end can be lowered. This allows separation of the compressed portions at the end to be prevented.

In a seventh aspect of the invention, in an absorbent article according to the sixth aspect of the invention, the weight of the low elasticity portion is less than or equal to 0.8 times the average weight of the absorbent body.

According to the seventh aspect of the invention, the amount of the absorbent material used can be made less by adjusting the weight of the low elasticity portion, which is less than or equal to 0.8 times the average weight of the absorbent body. This allows separation of the compressed portion at the end to be prevented by lowering the elasticity of the vicinity of the compressed portion.

In an eighth aspect of the invention, in an absorbent article according to any one of the first to the seventh aspects, the low elasticity portion is formed by pressurizing under normal or elevated temperature.

According to the eighth aspect of the invention, in the low elasticity portion formed by pressurizing under normal or elevated temperature, the thickness of the low elasticity portion can be made thin and at the same time, the lower elasticity can be achieved by compressing the low elasticity portions at a predetermined thickness. This allows separation of the compressed portion at the end to be prevented, by lowering the elasticity in the vicinity of the compressed portion at the end.

According to a ninth aspect of the invention, in an absorbent article according to any of the first through the eighth aspects, the absorbent article further includes a second sheet formed of a plurality of liquid permeable sheets which is laminated, the second sheet having a plurality of embossed compressed portions in the vicinity of the end, so as to be made less thick in the vicinity of the end.

According to the ninth aspect of the invention, the absorbent article further includes the second sheet formed from a plurality of the liquid permeable sheets which are laminated, and a second sheet having a plurality of embossed compressing portions in the vicinity of the end, so as to be made less thick in the vicinity of the end. This allows separation of the compressed portions in the end to be prevented, by lowering the elasticity in the vicinity of the compressed portion at the end.

In a tenth aspect of the invention, in an absorbent article according to any one of the first through the ninth aspects, the compressed portion, having a shape other than a substantially U shape, is disposed continuously along an outer periphery at the end of the absorbent article extending in a widthwise direction, by forming a linear or a curved line extending in a longitudinal direction. According to the tenth aspect of the invention, the compressed portion, having a shape other than a substantially U shape, is disposed continuously along the outer periphery at the end of the absorbent article, extending from the end initially in widthwise directions and then curving into longitudinal directions, by forming a linear or a curved line extending in the longitudinal direction, and normally, the width of the compressed portion in the vicinity of the end is small. In cases in which the low elasticity portion is disposed in the vicinity of the compressed portion, separation of the compressed portion at the end can be adequately prevented.

According to the present invention, there is provided an absorbent article having the compressed portion, formed of the liquid-proof grooves, to prevent separation of the compressed portion by achieving a superior leakage prevention performance and wearability.

BRIEF DESCRIPTION OF THE DRAWINGS

FIG. 4A to FIG. 4E are a diagram showing the cross section of the absorbent article according to FIG. 3;

FIG. 5 is a diagram showing a cross section of a compressed portion formed on the absorbent article according to the invention;

FIG. 6A and FIG. 6B are diagrams showing an embodiment of the absorbent article viewed from the top face, which is different from the embodiment shown in FIG. 1;

DETAILED DESCRIPTION OF THE INVENTION

Figure 1:
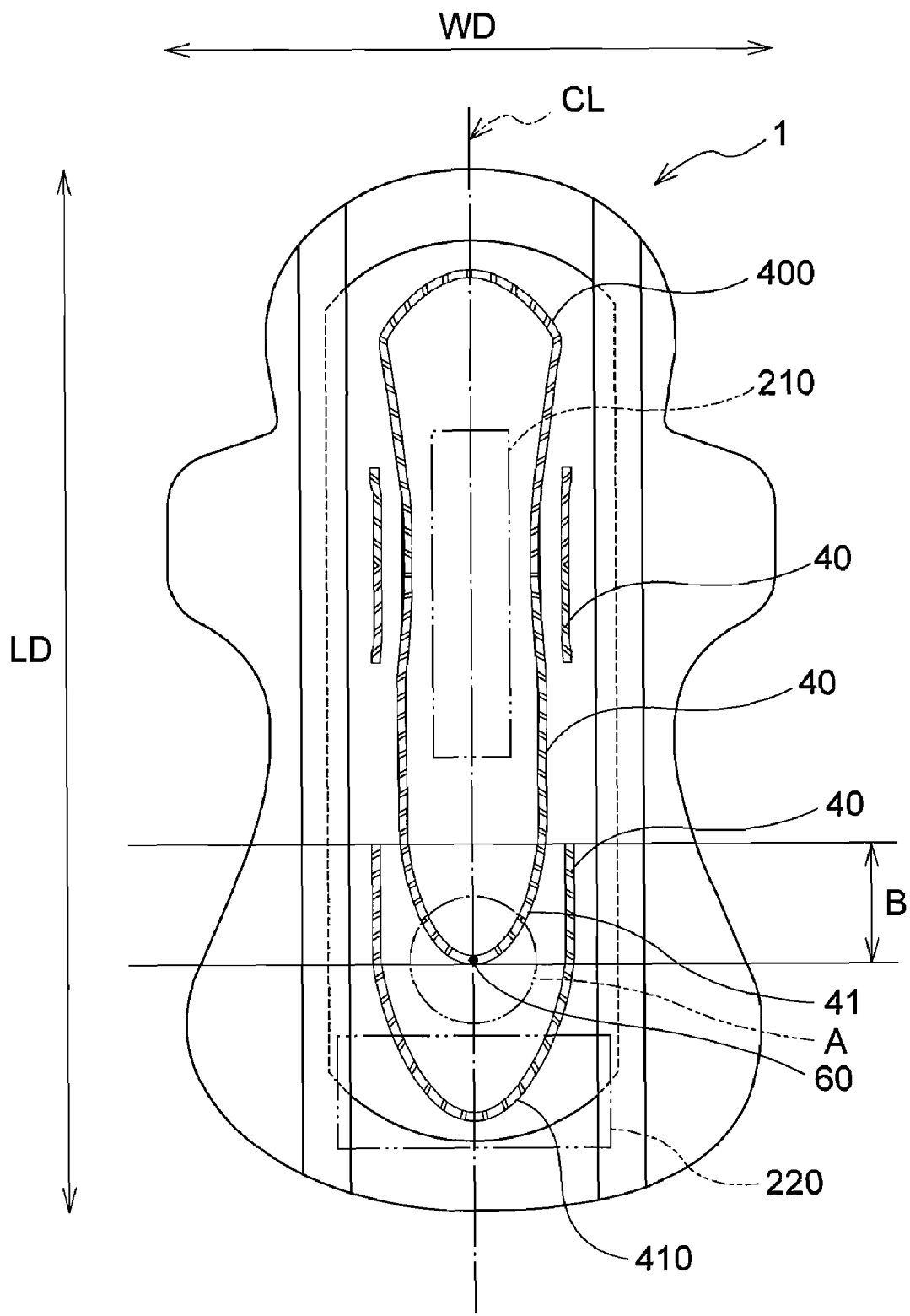
FIG. 1 is a diagram showing an absorbent article according to the invention viewed from the top face.
Figure 2:
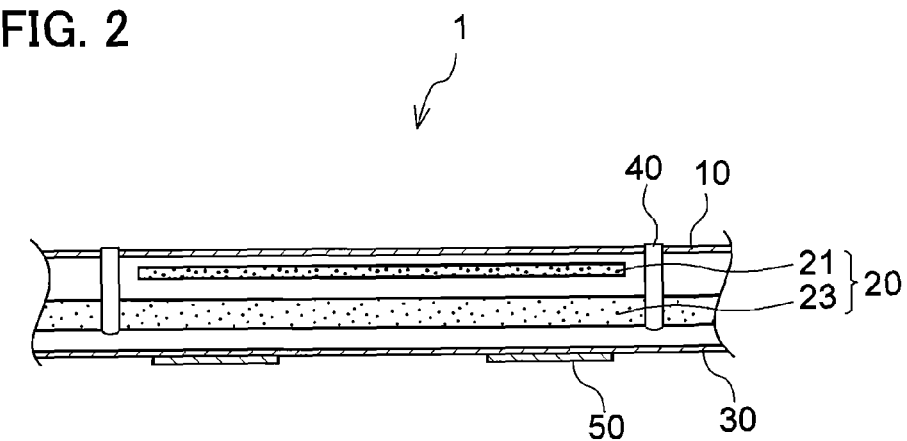
FIG. 2 is a diagram showing a cross section of the absorbent article according to the invention.
Figure 3:
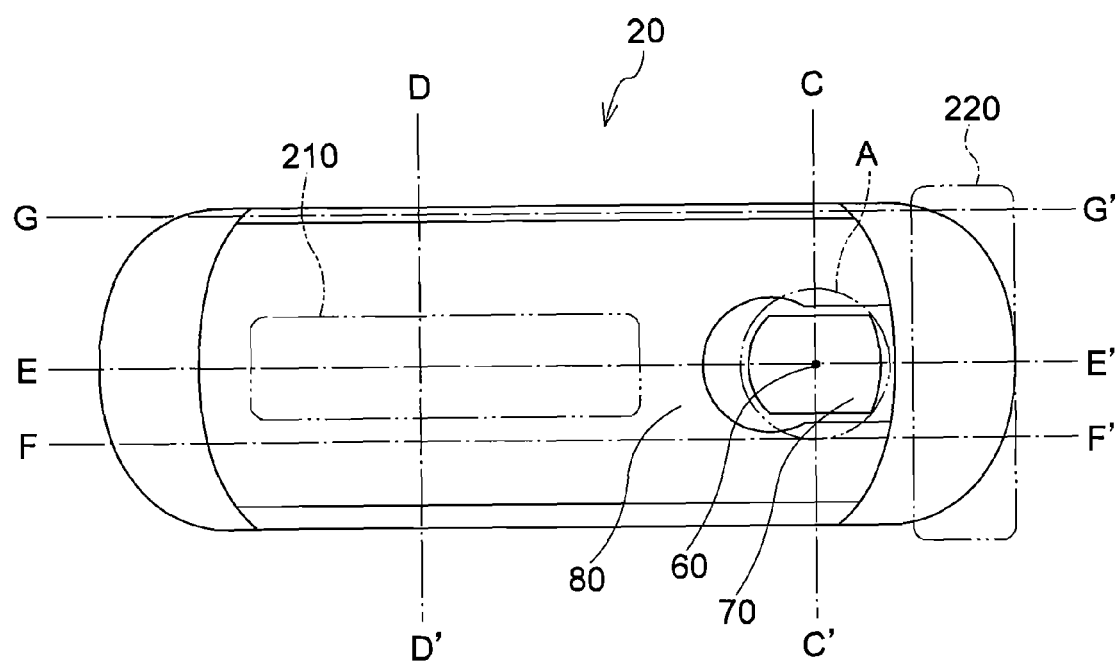
FIG. 3 is a diagram showing an absorbent article viewed from the top face.
Figures 7A, 7B, 7C:
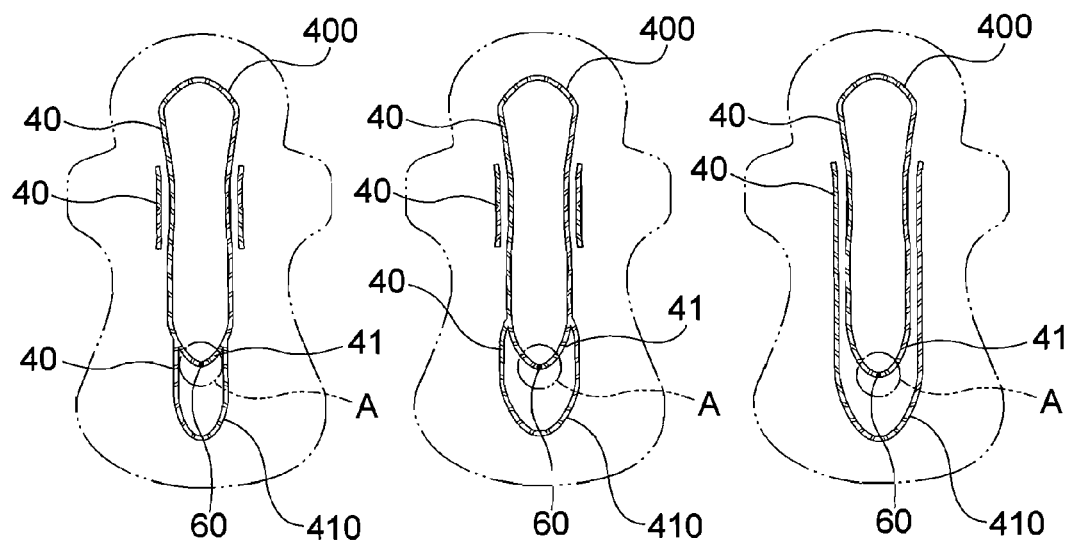
FIG. 7A to FIG. 7F are diagrams showing a modified embodiment of the absorbent article viewed from the top face.
Figures 7D, 7E, 7F:
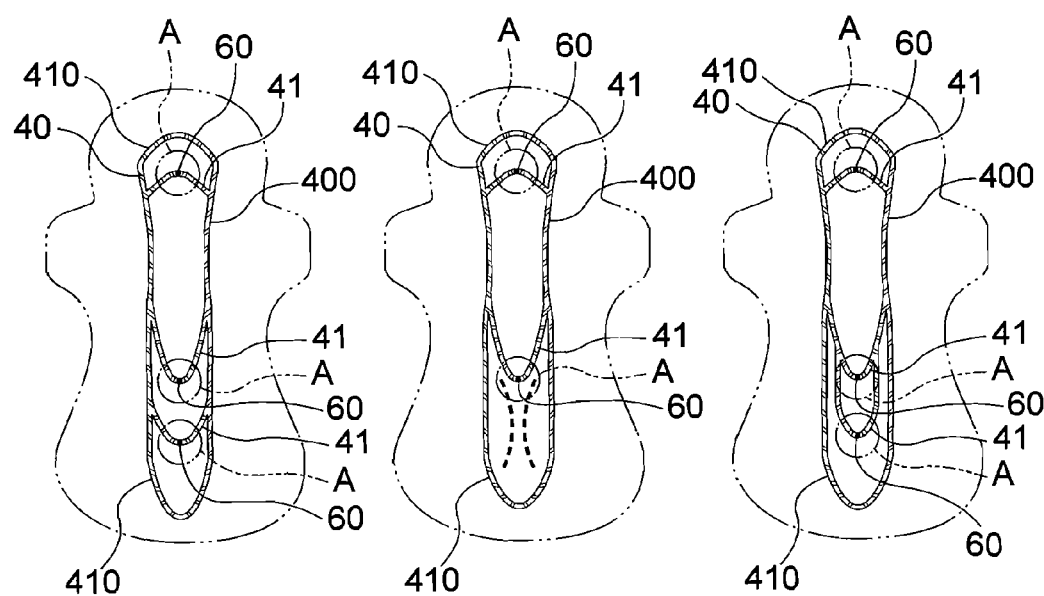
Figure 9A:
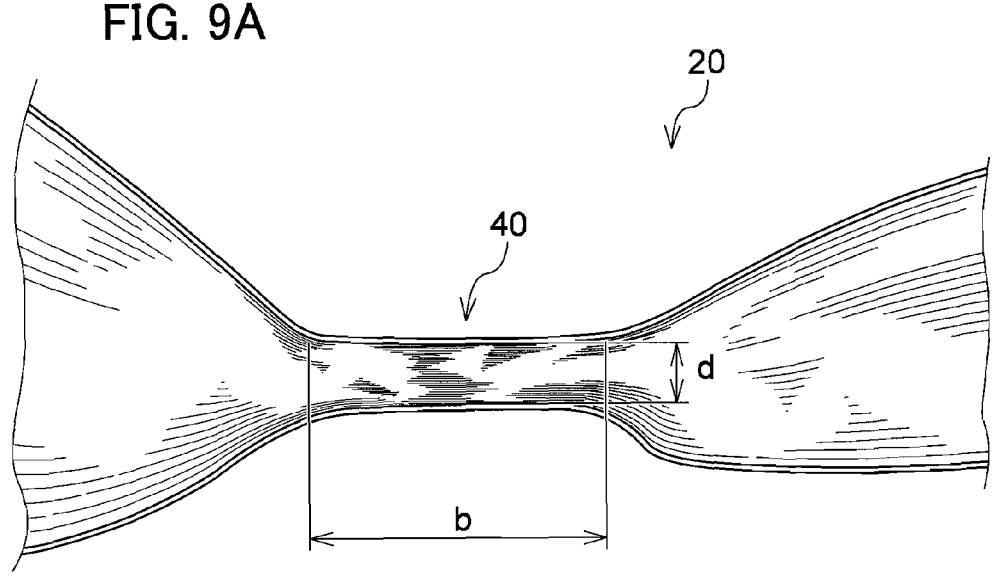
FIGS. 9A and 9B are diagrams showing an enlarged cross section of the compressed portion.
Figure 9B:
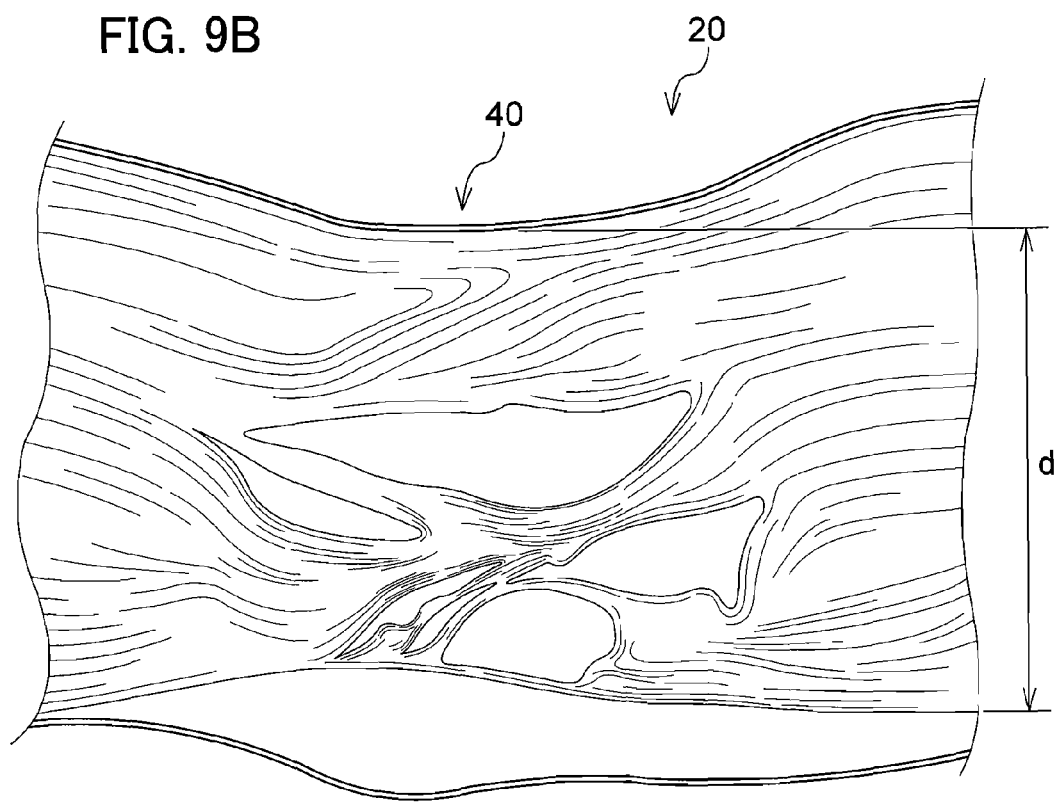
Figure 10A:
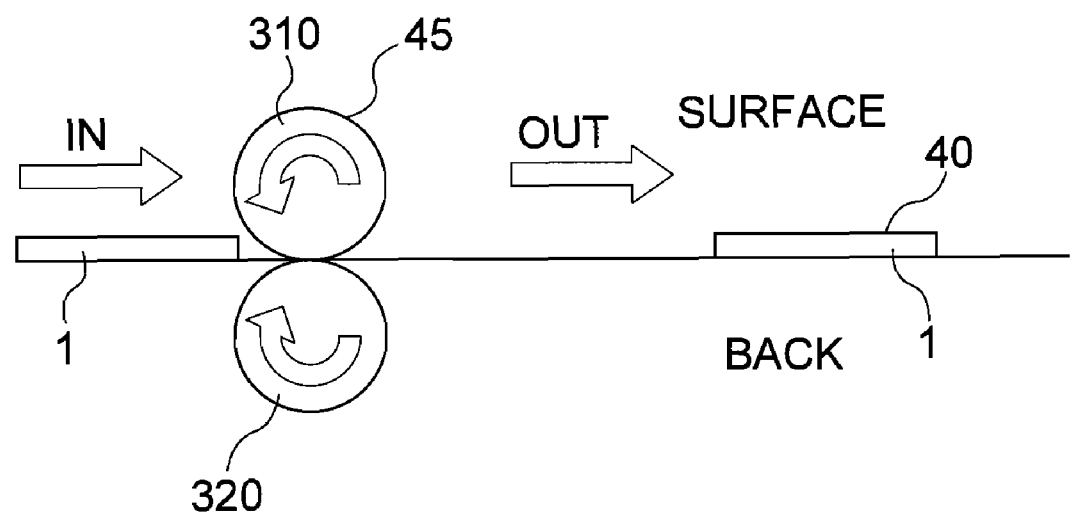
FIGS. 10A and 10B are diagrams showing a compression process of the absorbent article according to the invention, and a view, taken from the compressed side, of the absorbent article formed in the compression process.
Figure 10B:
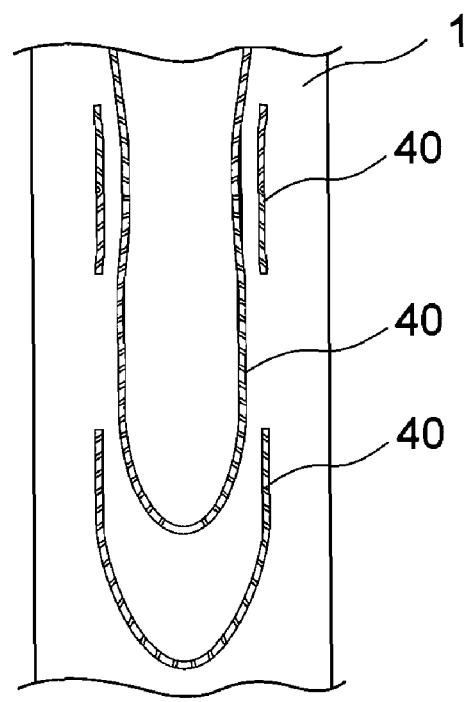
Figure 11:
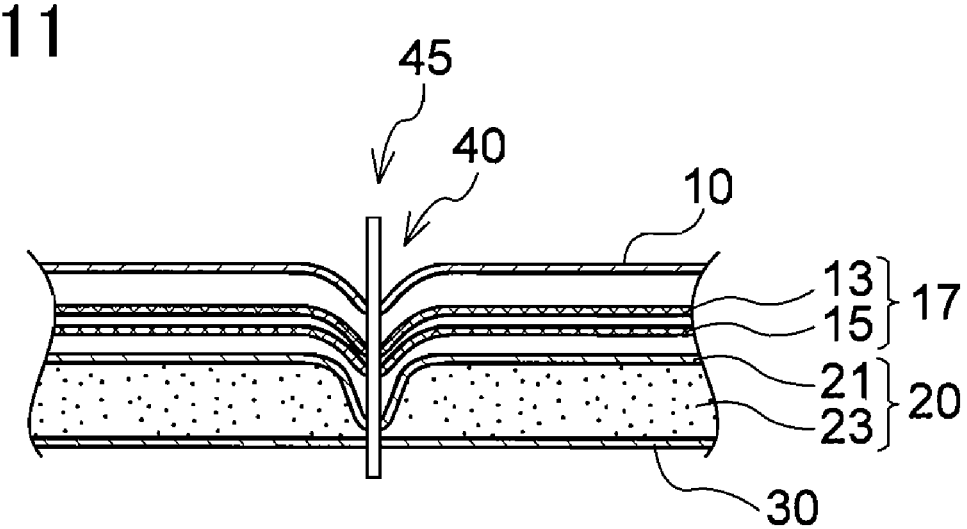
FIG. 11 is a diagram showing a cross section of a modified embodiment having a second sheet.
Figure 12A:
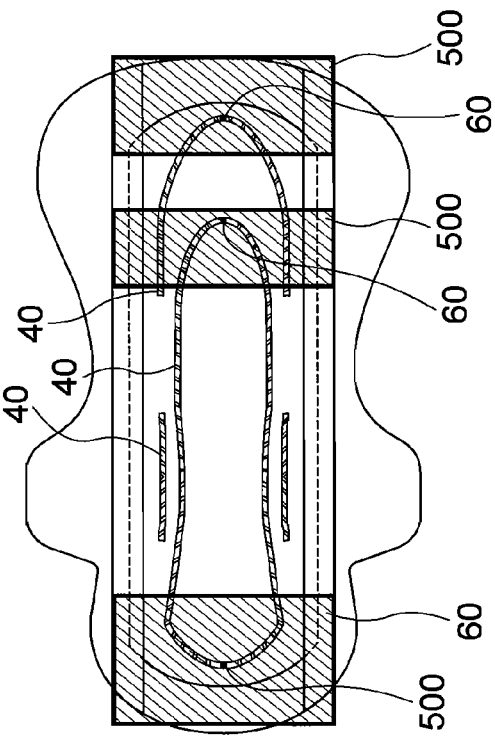
FIGS. 12A to 12C are diagrams showing an embossed compression portion in the second sheet.
Figure 12B:
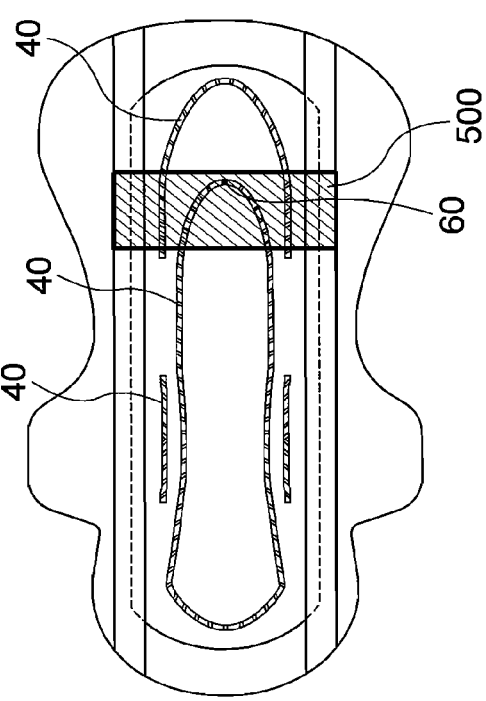
Figure 12C:
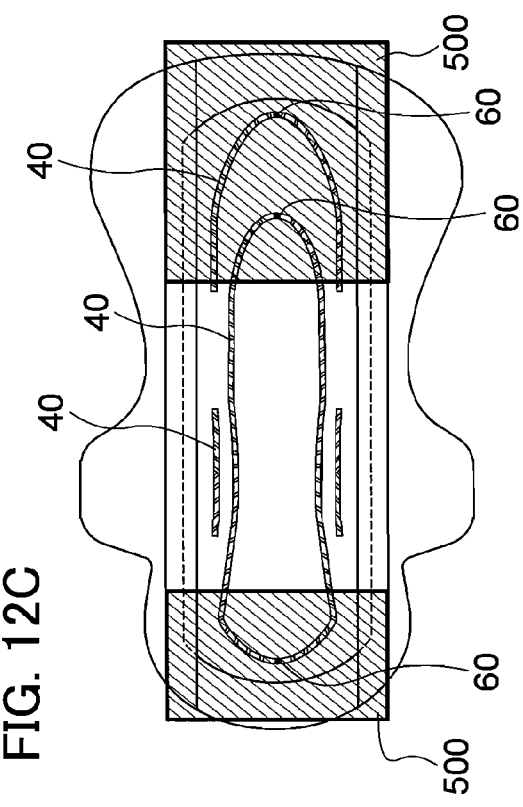
Figure 13:
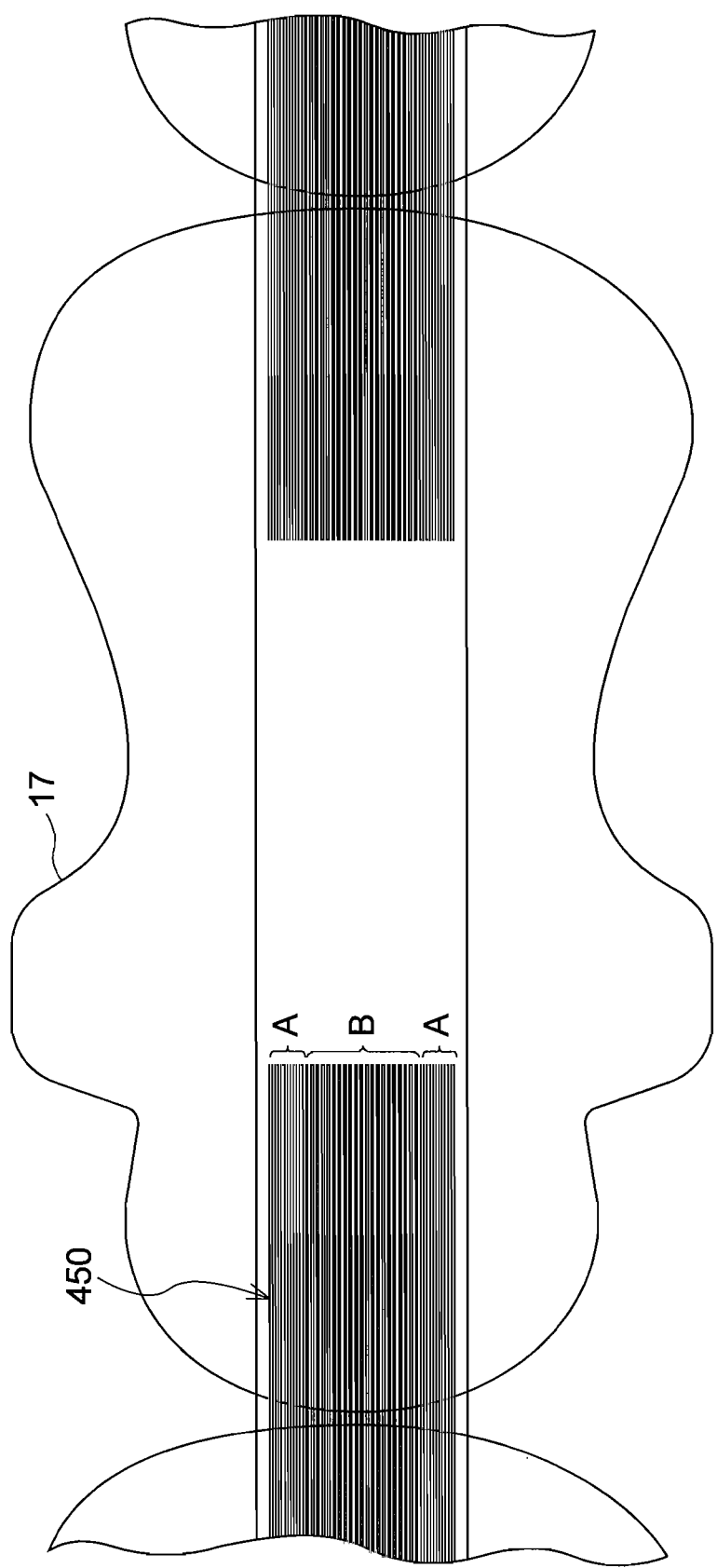
FIG. 13 is a diagram showing an applied state of hot-melt adhesive bonding a top sheet and the second sheet.
Figure 14:
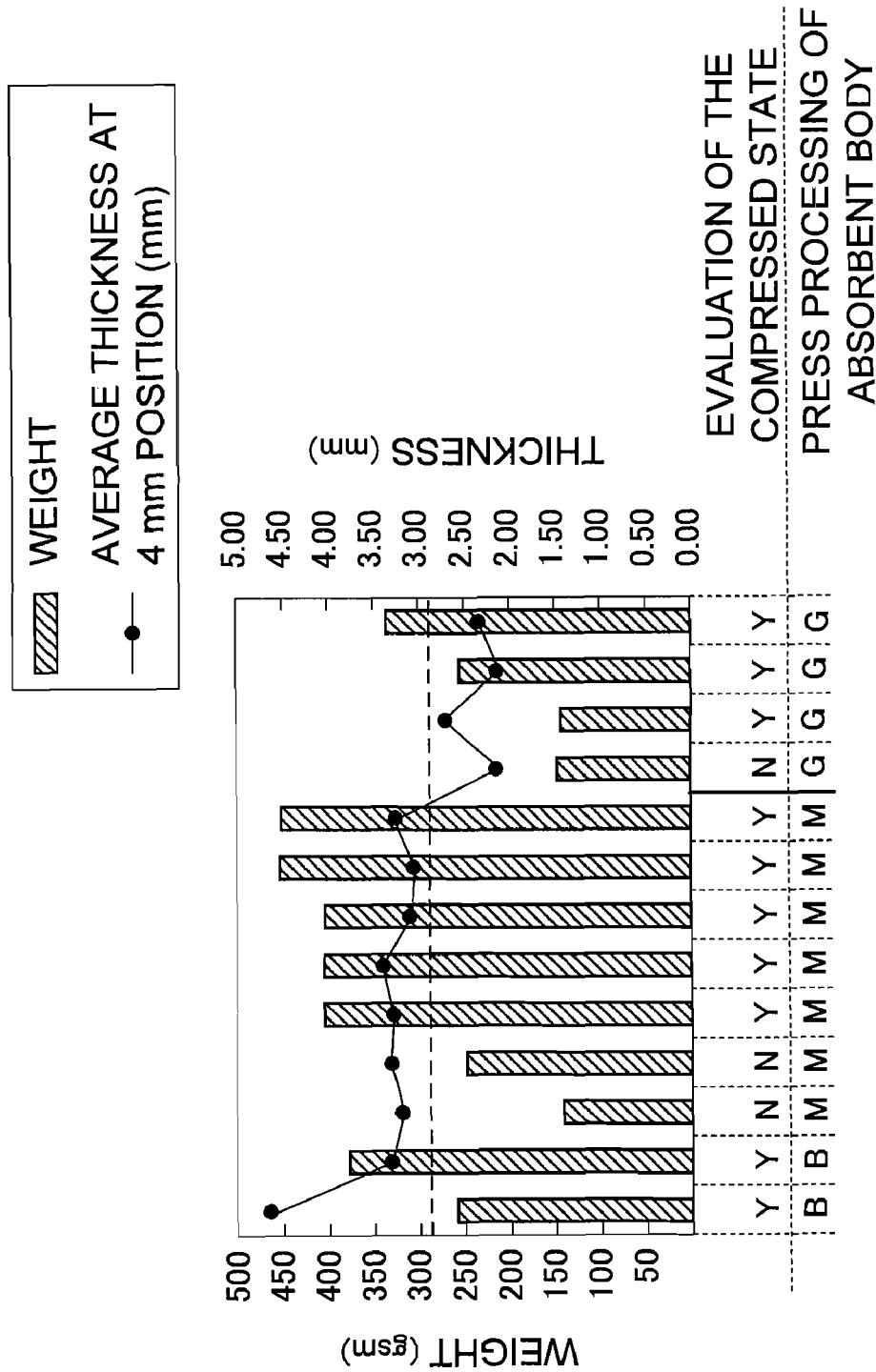
FIG. 14 is a graph presenting results of measurements and evaluations in examples.

The present invention will be discussed hereinafter in terms of the most preferred embodiments according to the present invention with reference to the accompanying drawings. FIG. 1 is a diagram showing a top view of an absorbent article according to the present invention. WD refers to widthwise direction, LD refers to longitudinal direction, and CL refers to centerline in this specification. FIG. 2 is a diagram showing a cross section of an absorbent article according to the present invention. FIG. 3 is a diagram showing a top view of an absorbent article. FIGS. 4A to 4E are diagrams showing a cross section of the absorbent article shown in FIG. 3. FIG. 5 is a diagram showing a cross section of a compressed portion formed on the absorbent article according to the present invention. FIGS. 6A and 6B are diagrams showing a top view of an absorbent article according to an embodiment which is different from FIG. 1. FIGS. 7A to 7F are diagrams showing a top view of a modified embodiment. FIGS. 8A to 8D are diagrams showing a state in which an elastic force is acting, when the top sheet and the absorbent body are compressed. FIGS. 9A and 9B are enlarged sectional views showing the compressed portion. FIG. 10A is a diagram showing a compression process of the absorbent article of the invention, and FIG. 10B is a diagram showing a top view of the absorbent article formed in the compression process viewed from the compression side. FIG. 11 is a diagram showing a cross-section of a modified embodiment having a second sheet. FIGS. 12A to 12C are diagrams showing a view of an embossed compressed portion in the second sheet. FIG. 13 is a diagram showing an applied state of hot-melt adhesive bonding a top sheet and the second sheet. FIG. 14 is a graph showing results of measurements and evaluations in examples. In the graph, Y refers to yes, No refers to No, and Yes means presence of the press processing, No means absence of press processing. B refers to bad, M refers to Medium, and G refers to Good.

(1) Overall Composition of the Absorbent Article

As shown in FIG. 1 and FIG. 2, the absorbent article 1 of the present invention, having a substantially oblong shape, includes a liquid-permeable top sheet 10, a back sheet 30, an absorbent portion 20 disposed between the top sheet and the back sheet, and compressed portions 40 in which the top sheet 10 and the absorbent portion 20 are pressed together. The back sheet 30 can be provided with an adhesive portion 50 that adheres to underwear or the like. In addition, the top sheet 10, the back sheet 30, and the absorbent portion 20 are each joined by a hot-melt adhesive.

The compressed portions 40 are arranged continuously to form a substantially U-shape 41 protruding in a longitudinal direction of the absorbent article. The compressed portions 40, as a whole, can be provided continuously in a substantially oval shape which includes a portion formed into the U-shape. In this case, the compressed portions 40, which are arranged continuously in a substantially oval shape, form a liquid-proof groove 400 to prevent an outflow of fluid absorbed in an absorbent portion 20.

As shown in FIG. 3, the absorbent portion 20 is provided with a low elasticity portion 70 which is included in a part of the absorbent body. The low elasticity portion 70 is formed so that elasticity occurring when compressed to a predetermined thickness becomes weak. The low elasticity portion 70, for example, is formed so that its resiliency (elasticity) becomes weak in comparison to resiliency (elasticity) occurring when the central portion 210 of the absorbent portion 20 and the adjacent contacting portions 80, described below, are compressed to the predetermined thickness.

The low elasticity portion 70 is arranged close to an end 60 that protrudes outwards to the largest extent in the longitudinal direction of the substantially U shape 41 formed by a compressed portion 40. The end 60, as shown in FIG. 1, is usually formed on a centerline in the longitudinal direction of the products, although this does not constitute a limitation. In addition, the vicinity of the end 60 refers to a predetermined region including the end 60, and, for example, it can be formed of an area including the region A formed of a substantially circular shape with the end 60 as center, as described below.

Here, for example, the compressed portion 40, as the liquid-proof groove 400 formed in the substantially oval shape, pressure-fixes the top sheet 10 and an absorbent portion at two points on each side in a widthwise direction. The end 60 is pressure-fixed substantially at one point. In other words, separation (lifting) of the compressed portion 40 at the end 60 easily occurs in comparison to other compressed portions 40. Separation (lifting) of the compressed portion 40 at the end 60 can be prevented by weakening the elasticity of the absorbent portion 20 crated in the vicinity of the compressed portion 40 by arranging the low elasticity portion 70 in the vicinity of the end 60 where the separation (lifting) easily occurs.

In addition, with the composition above, in the absorbent article 1 of the present invention, the compression maintenance index (k) of the compressed portion 40 at the end 60 may be greater than or equal to 80, preferably greater than or equal to 85, and more preferably greater than or equal to 90. In cases in which the compression maintenance index (k) is greater than or equal to 80, in the absorbent article 1 of the invention, the compression of the compressed portion 40 at the end 60 is sufficient, giving an impression, when viewed from a compressed side, that the compressed portion 40 has not lifted.

From FIG. 5, compression maintenance index (k) refers to a value calculated by dividing the width (b) of the compressed portion that has a thickness less than or equal to 0.5 mm, by the width (a) of the compressing part for forming compressed portions (for example, a convex part 45 formed on a compressing roller 310 in FIG. 10), and multiplying by 100, as described below in a formula 1.

$$k=(b/a)\times 100 \quad \text{(formula 1)}$$

(2) Low Elasticity Portions

As described above, the low elasticity portion 70 is formed so that when compressed to a predetermined thickness, the elasticity generated becomes weak. For example, the low elasticity portion 70 is formed so that its resilience (elasticity) weakens, in comparison to the resiliency generated when the central portion 210 of the absorbent portion 20 and an adjacent portion 80 are compressed to a predetermined thickness.

For example, as shown in FIG. 4A and FIG. 4C, the low elasticity portion 70 can be made very thin with respect to the adjacent portion 80 that is adjacent to the low elasticity portion 70. By reducing the thickness, resiliency (elasticity) generated upon compressing to a predetermined thickness can be made to weaken. Since the low elasticity portion 70 which is made thin is arranged in the vicinity of the end 60, separation (lifting) of the compressed portion 40 at the end 60 can be prevented by the resiliency (elasticity) generated by the absorbent portion 20 being compressed.

The low elasticity portion 70 is made very thin with respect to the adjacent portion 80, and at the same time, can also be made very thin with respect to the average thickness of an absorbent portion 20.

As shown in FIG. 3, the low elasticity portion 70 can be formed in a substantially circular shape, with the end 60 as center, and having a diameter of 10 to 50 mm, preferably of 20 to 40 mm, and more preferably of 25 to 35 mm. "Substantially circular" includes circular shapes or circle-based shapes modified to correspond to the shape of the absorbent article 1 and the absorbent portion 20.

The low elasticity portion 70, formed in a substantially circular shape with the end 60 as center and a diameter of 10 to 50 mm, can be made without excessively having reducing the volume of the absorbent portion 20. The absorbent portion 20 can favorably absorb body fluids such as menstrual blood. Therefore, both the separation of the compressed portion 40 at the end 60 can be prevented while achieving the liquid absorbency in the absorbent portion 20 at the same time.

In addition, as shown in FIG. 5, when the distance c from the compressed portion 40 at the end 60 is 4 mm, the low elasticity portion 70 is made very thin, with the thickness e of the absorbent portion 20 less than or equal to 2.5 mm, preferably less than or equal to 2.0 mm, and more preferably less than or equal to 1.8 mm. The low elasticity portion 70, is thus made thin in the vicinity of the end 60, such that resiliency (elasticity) occurring in the vicinity of the end 60 becomes weak. Therefore, separation (lifting) of the compressed portion 40 at the end 60 can be favorably prevented.

In addition, the amount of absorbent material used in forming the low elasticity portions 70, can be made less than the amount of absorbent material used in adjacent portions 80, and the elasticity can be weakened. Even when the density of the absorbent material in the low elasticity portion 70 is low, it has low elasticity since the amount of the absorbent material is small. Furthermore, by press-processing, as later described, it can be made even thinner.

For example, the weight of the low elasticity portion 70 can be made a factor of 0.8 or less times the average weight of the entire absorbent portion, preferably a factor of 0.7 or less, and more preferably a factor of 0.6 or less. In addition, as shown in FIG. 3, for example, the central portion 210 has a weight which can be from 500 to 600 g/m² (gsm), and the weight of the rear portion 220 from 300 to 400 g/m² (gsm), whereas the weight of the low elasticity portion 70 can be from 150 to 250 g/m² (gsm). When the shape of the absorbent portion 20 is complicated, or, although it is thin overall, the vicinity of the end 60 is made thick, the low elasticity portion 70 may be formed to have a lower weight with respect to the weight of the adjacent portions and the central portion, rather than the average weight.

In addition, the low elastic portions can be pressed, at a normal temperature or with heat added, to be made thinner. The low elasticity portion 70 can be made thinner by press-processing at normal temperature or with heat added. However, to make it thinner, press processing is preferably performed in a state heated to an extent at which the absorbent material does not deform. Here, as shown in TABLE 2 and FIG. 14 to be described below, the compression maintenance index becomes higher when the low elasticity portion becomes very thin, even with the same weight. In other words, it is desirable to make the low elasticity portion 70 very thin by press processing, so as to contribute to preventing separation (lifting) of the compressed portion 40 at the end 60.

(3) Compressed Portions and Liquid-Proof Groove

(3.1) Embodiment

As shown in FIG. 5, in the compressed portions 40, the top sheet 10 and the absorbent portion 20 are compressed. For example, as shown in FIG. 10A, the compressed portion 40 is passed between a compressing roller 310 having a predetermined convex portion 45 on its surface and a plane roll 320, while applying pressure, and is formed on the top face which is brought into contact with the compressing roller 310. The compressed portions 40 are preferably formed by press-processing under heat and pressure, and for example, press-processing can be performed by the compressing roller 310 at 95 degrees Centigrade (368.15 degrees K), and at a pressure of 25 kgm/s² (N). In addition, the width of the convex portion 45 which is the compressing portion for forming the compressed portions 40, varies according to embodiment of each product type, and, for example, press-processing can be done by the convex portion 45 with a width of 2.5 mm.

Figure 8A:
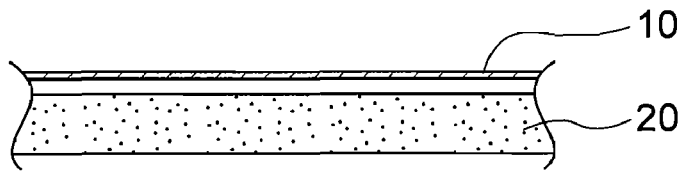
FIG. 8A to FIG. 8D are diagrams showing a state in which an elastic force is acting, when the top sheet and the absorbent body are compressed.
Figure 8B:
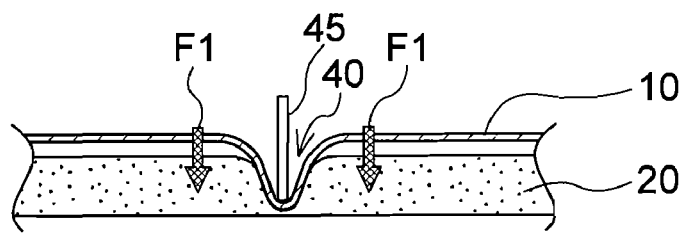
Figure 8C:
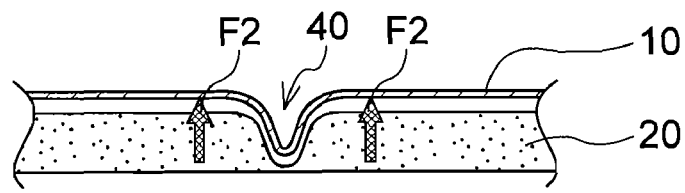
Figure 8D:
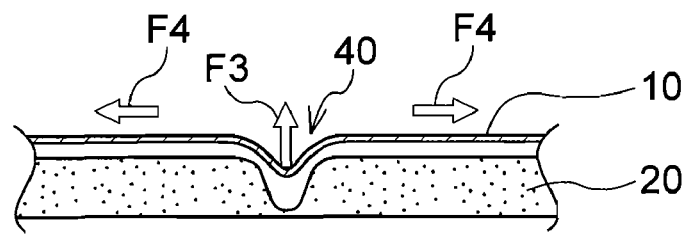

As shown in FIGS. 8A to 8D, the compressed portions 40, in a state in which the top sheet 10 and the absorbent portion 20 are arranged in a stacked layer, are formed by the convex portion 45 pressing from the top-sheet 10 face. As shown in FIG. 8B, when the compressed portion 40 is formed by the convex portion 45 pressing, a compressing force F1 is also added to the absorbent body 20 in the vicinity of the compressed portions 40, and the absorbent body 20 is compressed in the vicinity of the compressed portions 40. Subsequently, as shown in FIG. 8C, when the pressure imposed by the convex portion 45 is lifted, a resiliency (elasticity) F2 with which the absorbent body 20 compressed in the vicinity of the end 60 is restored, and the force is directed toward the direction of separating (lifting) the compressed portions 40. Further, as shown in FIG. 8D, a restoring force F4 for restoring the top sheet 10 drawn out in compression by the convex portion 45 is created, such that in the compressed portions 40, an additional force F3 is exerted in the direction where the compressed portion 40 is separated (lifted). In other words, in the compressed portion 40, it is found that the force is acting to continuously separate (lift) the compressed portion.

As shown in FIG. 5, the compressed portion 40 is pressure-bonded resulting in a width b and a thickness d. As described above, the force is exerted on the compressed portion 40 tending to separate (lift) this portion. When this force exceeds a force maintaining the compressed portion 40, the compressed portion 40 is separated such that the top sheet 10 is lifted. Particularly, the compressed portion 40 at the end 60 becomes easily separated (lifted) due to the forces exerted from various directions. However, in the absorbent article 1, the low elasticity portions 70 are provided in the vicinity of the end 60, where the force separating the compressed portion 40 becomes weak, such that the compressed portion 40 at the end 60 can maintain a favorable compressed state.

Specifically, the compressed portion 40 at the end 60 is formed for the purpose of achieving a compression maintenance index (k) of greater than or equal to 80, preferably of greater than or equal to 85, and more preferably of greater than or equal to 90. As shown in FIG. 5, the compression maintenance index (k) is a value calculated by dividing by the value of the width (a) of the convex portion 45 used for forming the compressed portions 40, the width (b) of the compressed portions having a thickness of less than or equal to 0.5 mm, and multiplying by 100, as described above in formula 1. When the compression maintenance index is greater than or equal to 80, bonding of the compressed portions 40 at the end 60 is sufficient, which would be seen as the compressed portions 40 not being lifted when viewed from the compressed side. In other words, as shown in FIG. 9A, the compressed portion 40 becomes firmly attached by pressure.

As stated above, for example, as shown in FIG. 1A, by passing through a press roller 310 having a predetermined convex portion 45 formed continuously on the surface, and a plane roller 320, while applying pressure, the compressed portions 40 are formed on the top face that is in contact with the press roll portion 310. By continuously passing the absorbent article 1, the compression-processing can be continuously performed. As shown in FIG. 10B, the compressed portions 40 are continuously formed in a predetermined shape through the press roller 310 having the convex portion 45 arranged in a pattern for forming the predetermined shape. For example, as described above, the compressed portions 40 form a liquid-proof groove 400 preventing the outflow of liquid from the absorbent body 20, when compressed portions are continuously provided in a substantially oval shape.

As shown in FIG. 1, the compressed portions 40 provided substantially at the center of the absorbent article 1 having a substantially oval shape are formed by surrounding a central portion 210 in an absorbent body 20. The end 60 in this oval shape is formed at the most protruding position of a continuously formed substantially U shape 41. This end 60 compresses and holds the absorbent body 20 substantively at one point in the widthwise direction. Since the compressed portions 40 at the end 60 become easily separated (lifted), in the present invention, the low elasticity portion 70 is formed, with, as reference, a circular region A having the end 60 as center.

In addition, as shown in FIG. 6, the pattern of compressed portions 40 can be formed differently from the formation pattern of compressed portions 40 shown in FIG. 1. In this case, separation (lifting) can be prevented by forming the low elasticity portion 70 in the vicinity of the compressed portions 40 at the end 60 of the substantially U shape 41. This low elastic portion 70, as earlier described, can be formed based on a circular region A by having as center the end 60.

(3.2) Modified Embodiment

As shown in FIG. 1, outside the compressed portions 40 continuously formed in a substantially oval shape in the substantially central portion of the absorbent article 1, another compressed portion 40 is arranged continuously so as to form a substantially U shape 410. Here, the compressed portion 40 for forming the outer substantially U shape 410, is formed in a widthwise direction at the end 60 outside of inner substantially U shape 41 of region B. In other words, the compressed portions 40 for forming the outer substantially U shape 410 are provided in a continuously manner so as to intersect with a line drawn in the widthwise direction from the end 60 of the inner substantially U shape 41, and it forms a straight line or a curve.

In region B, the liquid-proof grooves having at least three lines of the compressed portions 40 extending continuously in the widthwise direction are formed. As a compression force added during the compressing process becomes weak and the compression becomes insufficient, the region B of the compressed portions 40 causes to be easily separated (lifted). In other words, a force exerted by the press roller 310 (line pressure from continuous convex portion 45) is dispersed, and a force (line pressure) added to each compressed portion 40 deteriorates so that the compression force becomes weak. Particularly, the compressed portion 40 at the end 60 of the inner substantially U shape 41 becomes easily separated (lifted). In the invention, the low elasticity portion 70 is formed based on the circular region A which has the end 60 as center, to favorably prevent separation (lifting) of the compressed portions 40 at this end 60.

As shown in FIG. 7A to 7F, compressed portions 40 can be formed in a pattern which is different from a formation pattern of the compressed portions 40 of FIG. 1. Also in this case, separation (lifting) can be prevented, by forming the low elastic portion 70 based on the circular region A, in the vicinity of the compressed portions 40 at the end 60 that is the projecting portion with the substantially U shape 41. Particularly, when the low elastic portion 70 is formed in the vicinity of the end 60 which is provided by the outside of the compressed portions 40 formed in the substantially U shape 410, the separation (lifting) prevention effect is said to be large.

(4) Constituent Elements

A top sheet 10 is formed from a resin film in which a large number of liquid passage holes are formed, a net sheet having a large number of webs, a liquid permeable nonwoven fabric, or a cloth. The resin film and the net sheet can include materials formed from polypropylene (PP), polyethylene (PE) and polyethylene terephthalate (PET). In addition, a nonwoven fabric includes a cellulose fiber such as rayon, a spun lace nonwoven fabric formed from synthetic resin fiber, and a through-air nonwoven fabric formed from synthetic resin fiber, can be used. In addition, possible naturally biodegradable products such as polylactic acid, chitosan, polyalginic acid can be used. In addition, a large number of liquid passage holes can be formed, and water-repellent oil containing silicone and fluorine can be applied, so that body fluid does not easily adhere to the outer surface.

In addition, the weight is preferably from 15 to 100 $g/m^2$, and more preferably from 20 to 50 $g/m^2$. A core sheath structure of nonwoven fabric fiber having a bulk of from 0.4 to 2.0 mm, and further containing titanium oxide of greater than or equal to 1.0% in a core part, is less worn out during usage, and gains distance from the absorbent body 20. Furthermore, the top sheet 10 itself can also increase the concealment nature. In addition, there are advantageous effects for controlling diffusion of the top sheet 10 by adding 30% water-repellent fiber, and a curtailing effect on liquid absorption from the absorbent body 20 is obtained by blending water-repellent fiber. A sufficient surface strength is not achieved if the weight becomes less than or equal to 15 $g/m^2$, which may result in rupture during use. When the weight is greater than or equal to 100 $g/m^2$, roughness occurs and giving an uncomfortable sensation to the wearer during use. In addition, the density is not particularly limited so long as the density is less than or equal to 0.12 $g/cm^3$, and liquid permeable. If the density is greater than this, it becomes difficult for fluid to pass smoothly through between fibers of the top sheet. Since the viscosity of menstrual blood is higher than urine or the like, as low a density as possible is preferred.

In addition, when the top sheet 10 is an open pore film having a large number of liquid passage holes as described above, preferably, the pore diameter in a region straddling a folding line is in a range of 0.2 to 5 mm, pitch is in a range of 0.2 to 10 mm, and the open pore area is in a range of 10 to 50%, and the pore diameter outside the region straddling the folding line is preferably in a range of 0.05 to 3 mm, pitch in a range of 0.02 to 10 mm, and the open pore area is in a range of 3 to 30%. Manufacturing methods include passing the film through a pattern drum with pore conditions modified in advance, creating pores by suction, known as a PFW method, and a method in which pores are further added by pin emboss processing in the region straddling the folding line of the top sheet obtained through the PFW method which has uniform open pore conditions. The arrangement of the pores may be in a crosscheck pattern, a screen pattern, or a wavelike pattern, and is not particularly limited. In addition, the pore may have round, oval, or square shapes. In addition, a valve may be provided at a periphery of the pore region. Preferably, so that the pores are not easily blocked by the value even when external pressure is acting, the height of the valve of the pores in the region straddling the folding line in particular, is made lower than the height of the value s in regions other than that straddling the folding line. Here, because such an open pore film does not extend when compared with the non-woven material, the compressed portions 40 formed by the pore film become easily separated.

Material which can prevent leakage to the outside, of excretions absorbed by the absorbent body 20 can be used for the back sheet 30. In addition, by having moisture permeable material, sweatiness and discomfort can be reduced during wear. For example, such materials may include a composite sheet laminated from a liquid impermeable sheet mainly formed from polyethylene (PE) and polypropylene (PP), breathable film, non-woven fabric such as spun bond with liquid impermeable film on one side thereof. Specifically, to maintain flexibility without losing comfort in wearing, the liquid impermeable film can be formed mainly from low density polyethylene (LDPE) having its density in the range of 0.900 to 0.925 $g/cm^3$ with a weight of 15 to 40 $g/m^2$.

As shown in FIG. 11, a second sheet 17, formed by laminating the liquid permeable sheets 13 and 15, can additionally be disposed between the top sheet 10 and the absorbent body 20. The material used for the second sheet 17, can include a resin film having a large number of liquid permeable pores formed in a same manner as the top sheet 10, a net-type sheet having multiple webs (nets), a liquid permeable non-woven fabric, or woven fabric. Materials for resin film and the net-type sheet may include polypropylene (PP), polyethylene (PE), or polyethylene terephthalate (PET). In addition, the non-woven fabric can be formed of spun lace non-woven fabric made of cellulose fiber such as rayon, synthetic resin fiber, through-air non-woven fabric formed from the synthetic resin fiber, and the like. In addition, the second sheet 17 plays a role as a support for the absorbent body 20, by providing flexibility and formation stability to the absorbent body 20. For example, through-air non-woven fabric of 20 $g/m^2$ having an off-center core-sheath combined thermoplastic fiber (4 denier×50 mm) of polypropylene-polyethylene can be used as the second sheet 17. As an example, for a thickness of 1.0 to 2.0 mm, the density is from 0.015 to 0.01 $g/cm^3$.

In addition, as shown in FIG. 12, the second sheet 17 can be provided with the embossed compression portion 500 at a position in the vicinity of the end 60. The embossed compression portion 500 embossed at a predetermined region in the vicinity of the end 60 can be made thin, so that the region has low elasticity, which can further prevent the compressed portion 40 at the end 60 from separating.

The second sheet 17 is bonded to the top sheet 10 by predetermined hot-melt adhesive. For example, as shown in FIG. 3, a hot-melt adhesive is applied to the central portion 210 of the second sheet 17, as a plurality of thin lines extending in the longitudinal direction can be formed. For example, the coating patterns of the hot-melt adhesive can be shown in Table 1, below. According to a pattern 2, in comparison with a pattern 1, the second sheet 17 is tightly bonded to the top sheet 10, so as to be not easily separated. Although this does not greatly contribute to prevention of separation of the compressed portion 40 at the end 60 in the present invention, it contributes to formation stability in an absorbent 20, so that overall it contributes to the prevention of the separation of the compressed portion 40. In addition, bonding can be done so that the top sheet 10 and the second sheet 17 become thin which may contribute to preventing separation of the compressed portion 40 in the end 60.

TABLE 1

|  | Region A | | Region B | |
| --- | --- | --- | --- | --- |
|  | Thickness of applied portion × number of lines | Interval | Thickness of applied portion × number of lines | Interval |
| Pattern 1 | 0.75 mm for each of 6 lines | 0.7 mm | 0.5 mm for 18 lines | 1.0 mm |
| Pattern 2 | 0.75 mm for each of 6 lines | 0.7 mm | 0.5 mm for 21 lines | 0.8 mm |

As shown in FIG. 2, an absorbent body 20, which can be constructed from a cushion 21 and an absorber 23, is provided along the side of the top sheet 10. The absorbent material for the absorber 23 has a function to absorb and retain fluids such as menstrual blood, and is preferably bulky, not easily deformed, and with little chemical stimulation. In general, materials including wood-pulp, chemical pulp, rayon, acetate, natural cotton, an absorbent polymer, a fiber type absorbent polymer, a synthesized fiber, can be used alone or in a mixture. In addition, an absorptive sheet of air laid pulp, or nonwoven fabric containing absorptive fiber (spun lace, through-air method and the like) can be used. For example, liquid permeable paper and liquid permeable cellulose sheet are used as the cushion 21. One example, in which the absorbent body 20 is formed by combining the cushion 21 and the absorber 23, includes the pulp and the polymer having weights of 200 g/m² and 4 g/m² respectively (polymer is distributed throughout), uniformly distributed throughout in a mixture, surrounded by tissue having a weight of 15 g/m².

A form and a structure of the absorbent body 20 can be changed when required, although the total quantity absorbed by the absorber 23 should be in accordance with quantity the absorptive article is intended to take in, as well as the intended use. In addition, the size or the absorptive capacity of the absorber 23 is changed according to the wearer, from an infant to an adult.

As shown in the example above, an absorbent material having resiliency is used in the absorber 23. The compressed portion 40, having the top sheet 10 and the absorbent body 20 formed in a integrated manner, has a problem in that the compressed portion 40 separates, due to resiliency of the absorber 23 which is a component of the absorbent body 20. The problem is common for absorbent products such as sanitary napkins; to solve this problem, the absorbent article 1 of the present invention has the low elasticity portion 70, or the like.

As shown in FIG. 3, the absorbent body 20 is formed in a substantially elliptical or substantially rectangular shape, according to the patterned shapes of the absorbent article 1. This absorbent body 20 includes the center portion 210 which mainly absorbs liquid such as menstrual blood, and the low elasticity portion 70 at a location corresponding to the vicinity of the end 60. As shown in FIGS. 4B and 4C, the center portion 210 is formed to have bulk (thickness) in the direction of thickness. In addition, as shown in FIGS. 4B and 4D, a peripheral region 215 of the center portion 210 is formed to have bulk (thickness) in the direction of thickness, more than the other portions of the absorbent body 20. In contrast, the low elasticity portion 70 is made thin in the direction of thickness as shown in FIGS. 4A and 4C.

In addition, as shown in FIGS. 4A and 4C, the low elasticity portion 70 is made very thin with respect to the adjacent portion 80. As shown in FIG. 4A, the low elasticity portion 70, is made very thin in the direction of thickness with respect to the adjacent portion 80, in the widthwise direction. In addition, as shown in FIG. 4C, the low elasticity portion 70 is made very thin with respect to the adjacent portion 80 in the longitudinal direction. A front side face 71 is formed with a steep slope without being continuous with the shape of the adjacent portion 80, such that the low elasticity portion 70 is formed on the bottom side of the front side face 71. In addition, in the rear, a back side face 73 is formed with a steep slope without being continuous with the shape of the rear portion 220 (adjacent portion 80), such that the low elasticity portion 70 is formed on the bottom side of the front side face 73. Here, the low elasticity portion 70 can include faces such as the front side face 71 and the rear side face 73.

For other arrangements of the absorbent body 20, a rear portion 220 is formed at one end in the longitudinal direction, as shown in FIG. 3. The rear portion 220 is at a location at which thickness is smallest in the absorbent body 20 as shown in FIGS. 4C to 4E. In addition, as shown in FIG. 4E, the thickness at the edges in the widthwise direction of the absorbent body 20 is made thin similarly to the rear portion 220. Here, as shown in FIG. 4C, the low elasticity portion 70 can be made thinner than the rear portion 220.

Regarding the bonding portion 50, in addition to an adhesive agent such as an acrylic adhesive agent, or a rubber adhesive agent, a polyamino acid gel that may be cellulose based, polyvinyl alcohol based, gelatin, polyglutamic acid, or polylysine, that exhibit an adhesive force when in close contact with the skin, can be used.

(5) Example

Various low elastic portions were formed to examine effects for preventing separation of compressed portions of an absorbent article according to the embodiment. The results are shown below.

1. Conditions

Top sheet: The pore film formed by opening pores on the film of the following composition Composition: Low density polyethylene (MFR 15 g/10 min, density 0.915 g/cm³) 68%

: Low density polyethylene (MFR7 g/10 min, density 0.917 g/cm³)28%

: Titanic oxide 3.8%:

: Hydrophilic agent 0.2%

Weight: 25 g/m²

Opening ratio: 25%

Back sheet: Film composition made mainly from a low density polyethylene

Composition: Low density polyethylene (density 0.900-0.925 g/cm³) 87-99%

: Titanic oxide 2.6-3.2%

: Microdose coloring agent

Weight: 23.5 g/m²

Absorbent body: Made up of tissue-pulp-tissue (the pulp sandwiched between tissue)

Low elasticity portion

Shape: shown by the low elasticity portion 70 of FIG. 3 (Formed based on a circular region A)

Size: Diameter of circular region A is 30 mm (with end 60 as center)

Weight of pulp: Conditions stated in TABLE 2:

Press processing

Yes/No: See TABLE 2

Yes means presence of the press processing,

No means absence of press processing.

Pressure: 25 kg/s² (N)

Temperature: 95 degrees (368.15 K)

Conditions of compression: Compressed by press roll

Pressure: 25 kg/s² (N)

Temperature: 95 degrees (368.15 K)

Width of convex portion: 2.5 mm

2. Measurements and Evaluations

A compressed portion at the end 60 formed under the above conditions is cut along a center-line extending in the longitudinal direction, and the thickness at each location was measured as shown below. In addition, an evaluation of the compressed state was performed based on the results of the measurements. These results of the measurements and evaluations are presented in TABLE 2 and FIG. 14.

Measurement

Compressed portions: Width of compressed portions, with thickness less than or equal to 0.5 mm, was measured (width b of compressed portions when thickness d of compressed portions is less than or equal to 0.5, as shown in FIG. 5).

Vicinity of compressed portions: Thickness is measured at a location 4 mm away from the edge of compressed portions (The thickness e when c=4 mm, as shown in FIG. 5).

Measurement: Measured by microscope (manufactured by Keyence Corporation) at pressure-free state.

Evaluation of Compressed State

The evaluated was based on the compression maintenance index. The compression maintenance index was calculated by formula 1 based on the abovementioned measurement result.

According to the value of this compression maintenance index, the compression state was evaluated as follows.

Compression maintenance index 80 or more:
Assessment: good No lifting, as viewed from top face
Compressed maintenance index 20-80:
Assessment: medium: Portion of the compressed portions lifts, as viewed from top face
Compression maintenance index 20 or less:
Assessment: bad: The compressed portion lifts, as viewed from top face.

TABLE 2

| Evaluation of the compressed state | B | B | M | M | M | M | M | M | M | G | G | G | G |
|---|---|---|---|---|---|---|---|---|---|---|---|---|---|
| Press processing | Y | Y | N | N | Y | Y | Y | Y | Y | N | Y | Y | Y |
| Weight (g/m$^2$) | 253 | 375 | 138 | 244 | 402 | 402 | 402 | 452 | 452 | 142 | 139 | 252 | 332 |
| Average thickness at 4 mm position (mm) | 4.17 | 2.96 | 2.83 | 2.94 | 2.90 | 3.06 | 2.73 | 2.70 | 2.95 | 1.81 | 2.47 | 1.82 | 2.11 |

(B refers to bad, M refers to medium, G refers to good, Y refers to yes, N refers to no)

Analysis

From results of measurements and evaluations as shown in TABLE 2 and FIG. 14, separation (lifting) at the edges of the compressed portions can be favorably prevented by making the low elasticity portions thin. Particularly, by forming the low elasticity portions so that the thickness of the absorbent portion is 2.5 mm or less at a position 4 mm away from the edges of the compressed portions, the edges of the compressed portions can be favorably prevented from separating (lifting). In addition, separation (lifting) can be favorably prevented in the edges of the compressed portions, by reducing the weight of the absorbent body located in the vicinity of the edges. It was found to be possible to lower the elasticity by reducing the weight. Furthermore, separating (lifting) of the edges of the compressed portions can favorably be prevented by press processing. Even in the case of having the same weight, it was found that the thickness can be made very small, and since the elasticity can be reduced, elasticity reduction can be done.

What is claimed is:

1. An absorbent article having a substantially oblong shape comprising:
    a liquid permeable top sheet;
    a back sheet;
    an absorbent body having elasticity, disposed between the top sheet and the back sheet; and
    compressed portions compressing the top sheet and the absorbent body and comprising a first compressed portion and a second compressed portion disposed at an outer side of the first compressed portion,
    wherein the first compressed portion is disposed continuously so as to form a substantially U-shaped portion protruding in a longitudinal direction of the absorbent article, the substantially U-shaped portion being formed in a vicinity of an edge portion of the absorbent body and fixing the top sheet to the absorbent body by pressure bonding at substantially one point in an end of the substantially U-shaped portion that protrudes most in the longitudinal direction while not fixing the top sheet to the absorbent body in a portion other than at the one point, and, in a region including the end of the substantially U-shaped portion, the first and second portions extend substantially parallel to each other in the longitudinal direction and in a width direction perpendicular to the longitudinal direction,
    the absorbent body comprising:
    a low elasticity portion, disposed on a part of the absorbent body and formed so that resiliency weakens when compression to a prescribed thickness is carried out,
    wherein the low elasticity portion occupies a predetermined region including the end of said U-shaped portion and is formed to be substantially around the end of the substantially U-shaped portion that protrudes most in the longitudinal direction,
    wherein the low elasticity portion is thinner than an adjacent portion adjacent thereto and thinner than an average thickness of the absorbent body, and an amount of absorbent material forming the low elasticity portion is less than the amount of absorbent material in the adjacent portion.

2. The absorbent article according to claim 1, wherein the weight of the low elasticity portion is 0.8 or less times the average weight of the absorbent body.

3. The absorbent article according to claim 1, wherein the low elasticity portion is formed by pressing under a normal or increased temperature.

4. The absorbent article according to claim 1, further comprising a second sheet disposed between the top sheet and the absorbent body, and formed from a plurality of liquid permeable sheets being laminated, wherein the second sheet has a plurality of embossed compressed portions in the vicinity of the end.

5. The absorbent article according to claim 1, wherein the second compressed portion is disposed continuously along an outer periphery in the width direction at the end of the absorbent article, so as to form a straight or a curved line in the longitudinal direction.

6. An absorbent article having a substantially oblong shape comprising:
    a liquid permeable top sheet;
    a back sheet;
    an absorbent body having elasticity, disposed between the top sheet and the back sheet; and
    a compressed portion compressing the top sheet and the absorbent body forming a groove configured to inhibit the passage of liquid from one portion of the absorbent body to another portion of the absorbent body, said groove defining a closed elongated shape,
    the absorbent body comprising:
    a front side in a longitudinal direction of the absorbent body;
    a rear side in the longitudinal direction of the absorbent body opposing the front side;
    a center portion disposed between the front side and the rear side substantially center of the absorbent body in a width direction; wherein the rear side of the absorbent body is lower than the center portion in a thickness direction,
    a first low elasticity portion, disposed on a part of the absorbent body between the center portion and the rear side and formed so that resiliency weakens when compression to a prescribed thickness is carried out, as compared to the resiliency generated in an adjacent portion, and a second low elasticity portion disposed opposite to the first low elasticity portion in the longitudinal direction of the absorbent article, wherein an end of the elongated shape defined by said groove forms a substantially U shape protruding in the longitudinal direction of the absorbent article, wherein the first low elasticity portion is substantially circular in shape, has a diameter of 10 to 50 mm, and is substantially centered with respect to a bottom end of said U shape and with respect to a width direction of the absorbent article, wherein each of the first and second low elasticity portions is formed to be recessed from a surface of the top sheet, to have a bottom face surrounded by a side wall, and so that the weight of absorbent material forming the absorbent body portion in each low elasticity portion is less than the weight of absorbent material in the adjacent portion, wherein each of the first and second low elasticity portions is lower than the center portion in a thickness direction of the absorbent body, and lower than the rear side of the absorbent body, wherein a front edge of the first low elasticity portion is higher than a rear edge of the first low elasticity portion in the thickness direction of the absorbent body, wherein the side wall of each low elasticity portion is inclined down ward from the front edge and the rear edge toward the bottom face, wherein a compression maintenance index at the end is greater than or equal to 80, and wherein the first low elasticity portion has a thickness of 2.5 mm or less at a position 4 mm away in a longitudinal direction from the end.

* * * * *